United States Patent [19]

Saint-Leger et al.

[11] Patent Number: 5,939,077
[45] Date of Patent: *Aug. 17, 1999

[54] COSMETIC COMPOSITION COMPRISING A COMBINATION OF CERAMIDES AND USE THEREOF

[75] Inventors: Didier Saint-Leger, Courbevoie; Geneviève Kaba, Ivry Sur Seine; Georges Hussler, Aulnay Sous Bois, all of France

[73] Assignee: L'Oreal, Paris, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/600,543

[22] Filed: Feb. 13, 1996

[30] Foreign Application Priority Data

Feb. 15, 1995 [FR] France ................................. 95-01725

[51] Int. Cl.⁶ ..................................................... A61K 7/48
[52] U.S. Cl. ........................... 424/401; 424/61; 424/70.1; 514/844; 514/845; 514/846
[58] Field of Search .................................. 424/401, 70.1, 424/61; 514/844, 840

[56] References Cited

U.S. PATENT DOCUMENTS

| | | | |
|---|---|---|---|
| 5,149,860 | 9/1992 | Zysman et al. | 560/160 |
| 5,198,470 | 3/1993 | Zysman et al. | 514/785 |
| 5,476,661 | 12/1995 | Pillai et al. | 424/401 |
| 5,589,178 | 12/1996 | Aubert et al. | 424/401 |

FOREIGN PATENT DOCUMENTS

| | | |
|---|---|---|
| 420722 | 4/1991 | European Pat. Off. . |
| 0 500 437 | 8/1992 | European Pat. Off. . |
| 2679770 | 2/1993 | France . |
| 93/20038 | 10/1993 | WIPO . |
| 94/00127 | 1/1994 | WIPO . |

OTHER PUBLICATIONS

Abstract of JP–104286. Nov. 18, 1986.

Philip W. Wertz et al., "Composition of the Ceramides from Human Stratum Corneum and from Comedones", *Investigation Dermatology,* vol. 84, No. 5, pp. 410–412 (1985).

Mark A. Wiz et al., "Polar Lipid Composition of Mammalian Hair", *Comp. Biochem. Physiol,* vol. 36B. No. 4, pp. 671–673 (1987).

*Primary Examiner*—Jyothsna Venkat
*Attorney, Agent, or Firm*—Finnegan, Henderson, Farabow, Garrett & Dunner, L.L.P.

[57] ABSTRACT

The invention relates to a cosmetic composition comprising a mixture of ceramides, as well as to a process for treating the skin or keratin fibers that comprises applying to the skin or keratin fibers the cosmetic composition.

12 Claims, No Drawings

COSMETIC COMPOSITION COMPRISING A COMBINATION OF CERAMIDES AND USE THEREOF

The present invention relates to a novel cosmetic composition comprising a mixture of ceramides.

It is well known that hair which has been sensitized, that is to say damaged and/or embrittled to various degrees under the action of atmospheric agents or under the action of chemical or mechanical treatments, such as dyeing, bleaching and/or permanent-waving, is often difficult to disentangle and to style, and lacks softness. Indeed, under the action of these attacking factors (atmospheric agents, mechanical or chemical treatments), the hair loses some of its constituents such as, in particular, ceramides and proteins.

Ceramides or analogues thereof are known to protect and/or repair the skin and/or hair fibres from or after attack by the various agents and treatments mentioned above. In particular, they have a barrier effect which limits the loss of proteins; they also reinforce cuticle cohesion.

However, even though these ceramides prove to be effective, the protective or reparatory properties of compositions containing such compounds may still appear insufficient.

The aim of the invention is thus to propose improved cosmetic compositions, in particular cosmetic compositions having properties of limiting the loss of proteins. In point of fact, the Inventors have now discovered that a well-defined combination of ceramides makes it possible to achieve this aim.

The subject of the invention is thus a cosmetic composition, comprising, in a cosmetically acceptable medium, a mixture of ceramides comprising:

(a) at least one ceramide of formula (I):

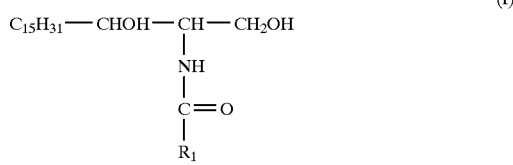

(I)

and (b) at least one ceramide chosen from the ceramides of formula (II):

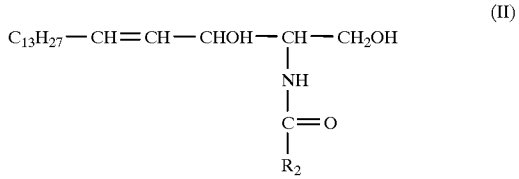

(II)

or of formula (III):

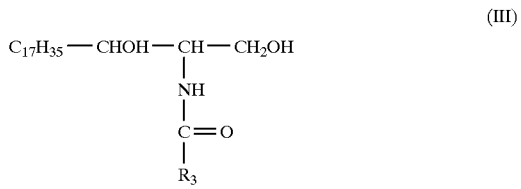

(III)

in which formulae $R_1$, $R_2$ and $R_3$, which may be identical or different, represent a linear or branched, saturated or unsaturated $C_{12}$–$C_{30}$, preferably $C_{14}$–$C_{26}$, hydrocarbon radical, which can be substituted with one or more hydroxyl groups.

Another subject of the invention is a process for treating the skin or keratin fibres, such as the hair, characterized in that it consists of applying to the said skin or to the said fibres cosmetic compositions according to the invention.

Preferably, the mixture of ceramides comprises several ceramides of formula (I) and several ceramides chosen from ceramides of formula (II) or of formula (III).

More preferably, the mixture of ceramides comprises at least one ceramide of formula (I), at least one ceramide of formula (II) and at least one ceramide of formula (III).

The mixture of ceramides used in the composition according to the invention preferably comprises at least one ceramide of formula (I) at a concentration of greater than or equal to 50% by weight relative to the total weight of the mixture of ceramides, and at least one ceramide chosen from ceramides of formula (II) or of formula (Ill) at a concentration of less than or equal to 50% by weight.

More preferably, the mixture of ceramides comprises from 65 to 90% by weight of at least one ceramide of formula (I) relative to the total weight of the mixture of ceramides and from 10 to 35% by weight of at least one ceramide chosen from ceramides of formula (II) or of formula (III) relative to the total weight of the mixture of ceramides relative to the total weight of the mixture of ceramides.

Even more preferably, the mixture of ceramides comprises, relative to the total weight of the mixture of ceramides, from 65 to 90% by weight of at least one ceramide of formula (I) from 6 to 20% by weight of at least one ceramide of formula (II) and from 4 to 15% by weight of at least one ceramide of formula (III).

The mixture of ceramides more preferably comprises, relative to the total weight of the mixture of ceramides, from 75 to 85% by weight of at least one ceramide of formula (I) and from 10 to 15% by weight of at least one ceramide of formula (II) and from 5 to 10% by weight of at least one ceramide of formula (III).

The mixture of ceramides most preferably comprises, relative to the total weight of the mixture of ceramides, 80% by weight of at least one ceramide of formula (I), 12% by weight of at least one ceramide of formula (II) and 8% by weight of at least one ceramide of formula (III).

The mixture of ceramides may also comprise at least one ceramide of formula (IV):

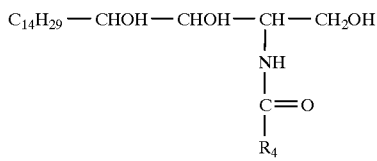

in which $R_4$ independently has the same meaning as that given for the radicals $R_1$, $R_2$ and $R_3$, preferably at a concentration ranging from 0 to 3% by weight relative to the total weight of the mixture of ceramides.

The radicals $R_1CO-$, $R_2CO-$, $R_3CO-$ and $R_4CO-$ are preferably independently chosen from radicals derived from myristic acid, palmitic acid, 2-hydroxypalmitic acid, stearic acid, eicosanoic acid, docosanoic acid, tetracosanoic acid, tetracosenoic acid and hexaco-sanoic acid, or derived from mixtures of such acids.

The radicals $R_1CO-$ and $R_2CO-$ more preferably represent, independently of each other, a mixture of radicals derived from myristic acid, palmitic acid, 2-hydroxypalmitic acid, stearic acid, eicosanoic acid, docosanoic acid, tetracosanoic acid, tetracosenoic acid and hexacosanoic acid.

The mixture of ceramides used in the composition according to the invention may be prepared by simple mixing of ceramides obtained synthetically.

The mixture of ceramides may also be extracted from head hairs or body hairs.

The concentration of the mixture of ceramides in the cosmetic composition according to the invention preferably ranges from 0.0001% to 10% by weight, approximately, relative to the total weight of the composition, preferably from 0.001 to 5% by weight and, more preferably, from 0.005% to 1% by weight.

The composition of the invention may also contain at least one additive chosen from thickeners, volatile or non-volatile and soluble or insoluble silicones, surfactants, fragrances, pearlescent agents, preserving agents, sunscreens, proteins, vitamins, polymers, plant, animal, mineral or synthetic oils and any other additive conventionally used in the cosmetics field.

These additives may be present in the composition according to the invention in proportions preferably ranging from 0 to 20% by weight relative to the total weight of the composition. The precise amount of each additive is readily determined by those skilled in the art according to its nature and its function.

Another subject of the invention is a process for treating the skin or keratin fibres, such as the hair, characterized in that it comprises applying to the skin or to the keratin fibres a cosmetic composition as defined above, optionally followed by rinsing with water.

Thus, this process according to the invention makes it possible to hold the hairstyle and to treat, care for, or wash the skin, the hair or any other keratinous material.

The cosmetic compositions according to the invention may be in the form of a gel, a milk, a cream, a more or less thickened lotion, a powder or a foam and may be used for the skin, for the hair, for the eyelashes or for the nails.

For the hair, they are more particularly shampoos, rinse-out or leave-in compositions, to be applied before or after shampooing, dyeing, bleaching, permanent-waving or straightening of the hair.

The compositions may also be hair-setting lotions, blow-drying lotions, fixing compositions (lacquers) and styling compositions. The lotions may be packaged in various forms, in particular in vaporizers, pump-dispenser bottles or in aerosol containers, so as to ensure application of the composition in vaporized form or in the form of a foam. Such packaging forms are indicated, for example, when it is desired to obtain a spray, a lacquer or a foam for fixing or treatment of the hair.

When the composition according to the invention is packaged in the form of an aerosol for the purpose of obtaining a lacquer or an aerosol foam, it preferably comprises at least one propellant, which may be chosen from volatile hydrocarbons such as n-butane, propane, isobutane, pentane, chlorinated and/or fluorinated hydrocarbons and mixtures thereof. Carbon dioxide, nitrous oxide, dimethyl ether, nitrogen or compressed air may also be used as a propellant.

In all of the text which follows and in the preceding text, the percentages expressed are weight percentages.

The invention will now be described in greater detail by means of the following examples, which are given solely by way of illustration and in no way limit the invention.

EXAMPLES

Example 1

Production of a Mixture of Ceramides Extracted from Hair 1.3 kg of washed and dried Caucasian brown hair was left to soak in 13 litres of heptane for 5 minutes. The hair was then placed in 8 litres of a mixture of dichloroethane/ethanol (2/1). The mixture was heated to 60° C. for 2 hours. The hair was next filtered and then placed in 8 litres of a dichloroethane/ethanol mixture (1/2) which was heated at 60° C. for 2 hours.

After evaporation of the solvents from the two extractions, 20–30 g of residue were obtained, which residue was chromatographed on a column of silica No. 60; 40–63 µm using fractions of a dichloromethane/-methanol mixture whose ratios varied from 100/0 to 50/50.

Only the 96/4 to 90/10 methanolic fractions were recovered, evaporated and dried. 1.6 g of residue were thus obtained.

The residue was analyzed by gas chromatography/mass spectrometry coupling.

The extracted residue comprised approximately 10% by weight of a mixture of ceramides consisting of:

- approximately 80% of ceramides of formula (I) in which $R_1,CO-$ represents a mixture of radicals derived from myristic acid, palmitic acid, 2-hydroxypalmitic acid, stearic acid, eicosanoic acid, docosanoic acid, tetracosanoic acid, tetracosenoic acid and hexacosanoic acid.
- approximately 12% of ceramides of formula (II) in which $R_2CO-$ represents a mixture of radicals derived from myristic acid, palmitic acid, 2-hydroxypalmitic acid, stearic acid, eicosanoic acid, docosanoic acid, tetracosanoic acid, tetracosenoic acid and hexacosanoic acid.
- approximately 8% of ceramides of formula (III) in which $R_3CO-$ represents a mixture of radicals derived from myristic acid, palmitic acid, 2-hydroxypalmitic acid, stearic acid, eicosanoic acid, docosanoic acid, tetracosanoic acid, tetracosenoic acid and hexaco-sanoic acid.

The mixture also contained a trace (<1% by weight) of ceramides of formula (IV) in which $R_4CO-$ represents a mixture of radicals derived from myristic acid, palmitic acid, 2-hydroxypalmitic acid, stearic acid, eicosanoic acid, docosanoic acid, tetracosanoic acid, tetracosenoic acid and hexacosanoic acid.

Example 2

The following four compositions were prepared:
Composition A: (invention)

| | |
|---|---|
| mixture of ceramides of Example 1 | 0.1 g |
| surfactant sold under the name REWOQUAT W75PG by the company Rewo | 0.5 g |
| water | qs 100 g |

Composition B: (placebo)

| | |
|---|---|
| surfactant sold under the name "REWOQUAT W75PG" by the company Rewo | 0.5 g |
| water | qs 100 g |

Composition C: (comparative)

| | |
|---|---|
| N-stearoyl phytosphingosine extracted from yeasts, sold by the company Gist-Brocades under the name "CERAMIDE III" | 0.1 g |
| surfactant | 0.5 g |
| water | qs 100 g |

Composition D: (comparative)

| | |
|---|---|
| sphingosine-containing glycosyl ceramides extracted from wheat flour, sold by the company Soliance under the name glycocéramides de blé [wheat glycoceramides] | 0.1 g |
| surfactant | 0.5 g |
| water | qs 100 g |

Each composition was applied to the washed hair, applying 2 g of composition per g of hair. The composition was left in place for 10 minutes. The hair was then rinsed thoroughly with water and dried.

For each lock treated, the amount of peptides released when the lock was immersed in water was determined. For this, 0.5 g of lock was immersed in 10 ml of distilled water for 15 minutes at 30° C.

The amount of proteins present in the water was then assayed: 1 ml of solution was placed in a counting flask, to which was added 1 ml of "Kit Micro BCA protein Assay Reagent" sold by the company Pierce. The flasks were then incubated in a water bath at 60° C. for 1 hour. After cooling to room temperature, the absorbance (optical density OD) at 562 nm was measured relative to water, using a 2100 UV spectrophotometer from Shimadzu. The amount of peptides present in each solution was determined using a calibration curve established with 8 solutions of albumin whose titre ranged from 2 µg/ml to 28 µg/ml.

The peptide concentration was calculated according to the following relationship:

$$C = \frac{OD - 0.00475}{0.04266}$$

The test was also carried out on untreated hair, by way of control.

The following results were obtained:

| Composition | Control | A (invention) | B (placebo) | C (comparative) | D (comparative) |
|---|---|---|---|---|---|
| Loss of peptides in µg/g of hair | 343 ± 3 | 261 ± 11 | 347 ± 24 | 302 ± 16 | 353 ± 15 |
| Rate of loss/control | 0% | −23.9% | +1.2% | −11.9% | +2.9% |

The results obtained show that only the hair treated with the composition according to the invention has the greatest decrease in the rate of loss of proteins.

Example 3

A shampoo having the following composition was prepared:

| | |
|---|---|
| mixture of ceramides of Example 1 | 0.1 g AM |
| sodium lauryl ether sulphate | 8 g |
| cocoylbetaine | 4 g |
| preserving agents | qs |
| fragrances | qs |
| sodium hydroxide (pH 6.8) | qs |
| demineralized water | qs 100 g |

This shampoo was applied repeatedly to wet hair: it affords better protection of the hair while at the same time limiting the loss of proteins.

Example 4

A cream having the following composition was prepared:

| | |
|---|---|
| mixture of ceramides of Example 1 | 0.25 g AM |
| glyceryl stearate | 2 g |
| sorbitan monostearate oxyethylenated with 20 mol of ethylene oxide | 1 g |
| stearic acid | 1.4 g |
| crosslinked polyacrylic acid sold under the name "CARBOPOL 940" by the company Goodrich | 0.4 g |
| liquid traction of karite butter | 12 g |
| triethanolamine | 0.7 g |
| perhydrosqualene | 12 g |
| fragrance | qs |
| antioxidant | qs |
| preserving agent | qs |
| demineralized water | qs 100 g |

We claim:

1. A cosmetic composition comprising, in a cosmetically acceptable medium, a mixture of ceramides comprising:

(a) from 65 to 90% by weight of at least one ceramide of formula (I):

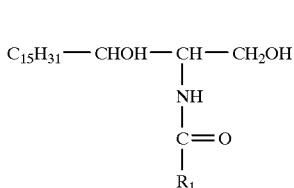

(b) from 6 to 20% by weight of at least one ceramide of formula (II):

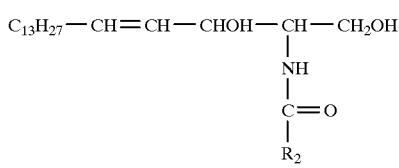

$$C_{13}H_{27}-CH=CH-CHOH-\underset{\underset{\underset{R_2}{C=O}}{NH}}{CH}-CH_2OH \quad (II)$$

and (c) from 4 to 15% by weight of at least one ceramide of formula (III):

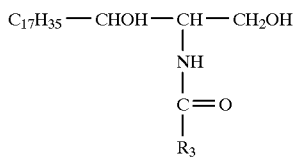

$$C_{17}H_{35}-CHOH-\underset{\underset{\underset{R_3}{C=O}}{NH}}{CH}-CH_2OH \quad (III)$$

wherein in said formulae (I), (II), and (III), the radicals $R_1CO—$, $R_2CO—$ and $R_3CO—$ are independently mixtures of radicals derived from myristic acid, palmitic acid, 2-hydroxypalmitic acid, stearic acid, eicosanoic acid, docosanoic acid, tetracosanoic acid, tetracosenoic acid and hexacosanoic acid.

2. A composition according to claim 1, wherein said mixture of ceramides comprises more than two ceramides of formula (I) and more than two ceramides of formula (II), or formula (III).

3. A composition according to claim 1, wherein the mixture of ceramides comprises, relative to the total weight of the mixture of ceramides, from 75 to 85% by weight of at least one ceramide of formula (I), from 10 to 15% by weight of at least one ceramide of formula (II), and from 5 to 10% by weight of at least one ceramide of formula (III).

4. A composition according to claim 3, wherein the mixture of ceramides comprises, relative to the total weight of the mixture of ceramides, 80% by weight of at least one ceramide of formula (I), 12% by weight of at least one ceramide of formula (II), and 8% by weight of at least one ceramide of formula (III).

5. A composition according to claim 1, wherein the mixture of ceramides further comprises from 0 to 3% by weight, relative to the total weight of the mixture of ceramides, of a ceramide of formula (IV):

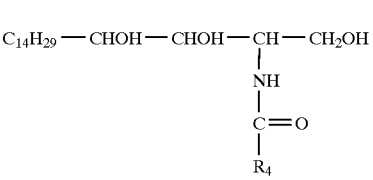

$$C_{14}H_{29}-CHOH-CHOH-\underset{\underset{\underset{R_4}{C=O}}{NH}}{CH}-CH_2OH \quad (IV)$$

in which $R_4$ denotes a linear or branched, saturated or unsaturated $C_{12}$–$C_{30}$ hydrocarbon radical, which can be substituted with one or more hydroxyl groups.

6. A composition according to claim 5, wherein the radical $R_4CO—$ is a radical derived from myristic acid, palmitic acid, 2-hydroxypalmitic acid, stearic acid, eicosanoic acid, docosanoic acid, tetracosanoic acid, tetracosenoic acid or hexacosanoic acid.

7. A composition according to claim 1, wherein the concentration of the mixture of ceramides is from 0.0001% to 10% by weight relative to the total weight of the composition.

8. A composition according to claim 7, wherein the concentration of the mixture of ceramides is from 0.001% to 5% by weight relative to the total weight of the composition.

9. A composition according to claim 1, wherein the mixture of ceramides is derived from a mixture of synthetic ceramides.

10. A composition according to claim 1, wherein the mixture of ceramides is extracted from head hair or body hair.

11. A process for treating the skin or keratin fibres, comprising the step of applying to the skin or to the fibres a cosmetically effective amount of a cosmetic composition according to claim 1.

12. A process for treating hair, comprising the step of applying to the hair a cosmetic composition according to claim 1.

* * * * *

UNITED STATES PATENT AND TRADEMARK OFFICE
CERTIFICATE OF CORRECTION

PATENT NO.:      5,939,077
DATED:           August 17, 1999
INVENTOR(S):     Didier Saint-Leger et al.

It is certified that an error appears in the above-identified patent and that said Letters Patent is hereby corrected as shown below:

Claim 5, col. 8, line 14, "$Cl_2-C_{30}$" should read --$C_{12}-C_{30}$--.

Signed and Sealed this

Sixteenth Day of November, 1999

Attest:

Q. TODD DICKINSON

Attesting Officer

Acting Commissioner of Patents and Trademarks